(12) United States Patent
Golden

(10) Patent No.: US 6,727,388 B2
(45) Date of Patent: Apr. 27, 2004

(54) DEMULSIFYING COMPOUND AND A METHOD OF BREAKING OR INHIBITING EMULSIONS

(75) Inventor: Robert Golden, Santa Fe Springs, CA (US)

(73) Assignee: Pilot Chemical Holdings, Inc., Sante Fe Springs, CA (US)

( * ) Notice: Subject to any disclaimer, the term of this patent is extended or adjusted under 35 U.S.C. 154(b) by 0 days.

(21) Appl. No.: 10/358,995

(22) Filed: Feb. 4, 2003

(65) Prior Publication Data

US 2003/0130534 A1 Jul. 10, 2003

Related U.S. Application Data

(62) Division of application No. 09/696,629, filed on Oct. 24, 2000, now Pat. No. 6,545,181.

(51) Int. Cl.[7] .................. C09K 3/00; C07C 309/00; C07C 211/62; C07C 211/64; C07F 7/02

(52) U.S. Cl. .................. 564/291; 564/282; 562/30; 562/400; 556/410; 516/144; 516/145; 516/152; 516/153; 516/181; 516/186

(58) Field of Search .................. 564/291, 282; 516/145, 152, 153, 186

(56) References Cited

U.S. PATENT DOCUMENTS

| 2,226,118 | A |   | 12/1940 | De Groot |          |
|-----------|---|---|---------|----------|----------|
| 3,215,620 | A |   | 11/1965 | Dunning et al. | |
| 3,228,758 | A |   | 1/1966  | Bauer et al. | |
| 3,925,442 | A |   | 12/1975 | Samour |            |
| 4,416,796 | A |   | 11/1983 | Böhm et al. |     |
| 4,439,345 | A |   | 3/1984  | Duke |              |
| 5,154,857 | A |   | 10/1992 | Durrieu et al. | |
| 5,962,726 | A | * | 10/1999 | Kwetkat et al. | 560/171 |
| 5,977,404 | A |   | 11/1999 | Kwetkat et al. | |
| 5,997,610 | A |   | 12/1999 | Kwetkat et al. | |
| 6,034,271 | A | * | 3/2000  | Kwetkat | 562/565 |
| 6,066,755 | A | * | 5/2000  | Koch et al. | 558/266 |
| 6,545,181 | B1|   | 4/2003  | Golden |           |

FOREIGN PATENT DOCUMENTS

| DE | 24 34 545   | 1/1976 |
| EP | 0 644 250 A | 3/1995 |
| GB | 789779      | 1/1958 |
| WO | WO 96/16033 | 5/1996 |
| WO | WO 96/25393 | 8/1996 |
| WO | WO 97/02234 | 1/1997 |
| WO | WO 97/22577 | 6/1997 |

OTHER PUBLICATIONS

Partial European Search Report for European Application No. EP 01 12 5162, Apr. 11, 2003, 7 pages.

Database Crossfire Beilstein 'Online! Beilstein Institut zur Förederung der Chemischen Wissenschaften, Frankfurt am Main, DE; Database accession No. 7106429, XP002238021, & Ito, M. et al: Bulletin of the Chemical Society of Japan, vol. 62, No. 12, 1989, pp. 3919–3922, Japan Publications Trading Co. Tokyo, JP ISSN: 0009–2673. (Abstract).

Database Crossfire Beilstein 'Online! Beilstein Institut zur Förederung der Chemischen Wissenschaften, Frankfurt am Main, DE; Database accession No. 7107248, XP002238020, & Ito, M. et al: Bulletin of the Chemical Society of Japan, vol. 62, No. 12, 1989, pp. 3919–3922, Japan Publications Trading Co. Tokyo, JP ISSN: 0009–2673. (Abstract).

Database Crossfire Beilstein 'Online! Beilstein Institut zur Förederung der Chemischen Wissenschaften, Frankfurt am Main, DE; Database accession No. 6458510, XP002238019 & Shibata, O et al: Bulletin of the Chemical Society of Japan, vol. 55, No. 7, 1982, pp. 2243–2247, Japan Publications Trading Co. Tokyo, JP ISSN: 0009–2673. (Abstract).

Database Crossfire Beilstein 'Online! Beilstein Institut zur Förederung der Chemischen Wissenschaften, Frankfurt am Main, DE; Database accession No. 6992514, XP002238018, & Shibata. O et al: Bulletin of the Chemical Society of Japan, vol. 61, 1988, pp. 3077–3082, Japan Publications Trading Co. Tokyo, JP ISSN: 0009–2673. (Abstract).

Database Crossfire Beilstein 'Online!Beilstein Institut zur Förederung der Chemischen Wissenschaften, Frankfurt am Main, DE; Database accession No. 8460644, XP002238017, & Abramzon, A A: Russian Journal of Applied Chemistry, vol. 72, No. 4, 1999, pp. 666–669, Consultants Bureau, US, ISSN: 1070–4272. (Abstract).

Database Crossfire Beilstein 'Online! Beilstein Institut zur Förederung der Chemischen Wissenschaften, Frankfurt am Main, DE; Database accession No. 6458849, XP002238016 & Jokela, P. et al: Journal of Physical Chemistry, vol. 91, No. 12, 1987, pp. 3291–3298, American Chemical Society, US, ISSN: 0022–3654. (Abstract).

Database Crossfire Beilstein 'Online! Beilstein Institut zur Förederung der Chemischen Wissenschaften, Frankfurt am Main, DE; Database accession No. 3746255, XP002238015, & Borick et al.: Applied Microbiology, vol. 7, 1959, pp. 248, Washington, DC, US. (Abstract).

(List continued on next page.)

*Primary Examiner*—Brian Davis
(74) *Attorney, Agent, or Firm*—Michael J. Wise; Perkins Coie LLP

(57) ABSTRACT

The present invention is a demulsifying and corrosion-inhibiting compound formed from the salt of an amphiphilic amine and an amphiphilic acid. In a preferred embodiment of the invention, the demulsifier may be a salt of an alkyl amine and an alkyl aryl sulfonic acid. Even more preferably, the demulsifier may be a salt of a methyl, di-cocoyl amine and an alkyl aryl sulfonic acid. According to another embodiment of the invention, an organic system may be demulsified by mixing the salt of an alkyl amine and an alkyl sulfonic acid with the system to be demulsified.

27 Claims, No Drawings

OTHER PUBLICATIONS

Database Crossfire Beilstein 'Online! Beilstein Institut zur Förederung der Chemischen Wissenschaften, Frankfurt am Main, DE; Database accession NO. 3751833, XP002238014, & Jokela, P. et al: Journal of Physical Chemistry, vol. 91, No. 12, 1987, pp. 3291–3298, American Chemical Society, US, ISSN: 0022–3654. (Abstract).

Database Crossfire Beilstein 'Online! Beilstein Institut zur Förederung der Chemischen Wissenschaften, Frankfurt am Main, DE; Database accession No. 3800155, XP002238013, & Hunter: Iowa State Coll.J.Sci., vol. 15, 1941, pp. 228–230. (Abstract).

*Database CAPLUS on STN, Acc. No. 1993:633501, QIU et al., Determination of nitrate–N and Nitrite–N in surface water by highly sensitive spectrophotometric method. Huanjing Kexue (1992), 13(4), P. 63–6 (Abstract).

* cited by examiner

DEMULSIFYING COMPOUND AND A METHOD OF BREAKING OR INHIBITING EMULSIONS

This Application is a Division of U.S. patent application Ser. No. 09/696,629 filed Oct. 24, 2000, now U.S. Pat. No. 6,545,181 and now pending and which is incorporated herein by reference. Priority to this application is claimed under 35 U.S.C. §120.

BACKGROUND OF THE INVENTION

1. Field of the Invention

This invention relates to chemical compounds.

2. Background

Demulsifying agents break emulsions of polar solutes like water, and non-polar solvents like oil. They are used in functional fluids (such as, but not limited to, metal removal fluids, greases, rust and oxidation fluids, hydraulic oils, compressor oils, fuels and transformer fluids) to inhibit formation of emulsions, break emulsions that have developed, and to inhibit corrosion.

Among their industrial uses, demulsifiers are commonly used to dehydrate and desalt crude oil during refinement. Typically, in order to remove sedimentation found in crude oil, crude oil is treated with soda ash and water. This salt and water, unless removed, will cause problems in distillation columns. The salt will foul the heat exchangers and the water may vaporize, possibly causing an explosion. To remove the salt and water, the crude oil is treated with demulsifying agents.

In the closed, harsh environment of hydraulic systems, demulsifiers must be effective at high temperatures, often in excess of 300° C. Failure of a demulsifier in a hydraulic system may lead to catastrophic failure. Demulsifiers are also frequently put to use in hydraulic systems to prevent corrosion. In the presumed mechanism of corrosion inhibition, the demulsifier adsorbs on the metal surface forming a protective film against polar solutes. More preferably still, demulsifiers in such systems are ashless to avoid clogging filters and orifices. Calcium sulfonates, though not ashless, are common demulsifiers in hydraulic systems.

Demulsifiers are added to fuel systems to prevent water from interfering with the combustion process. Like in hydraulic systems, demulsifiers used in fuel systems should preferably be ashless to avoid deposits.

In their broadest conception, demulsifiers are made out of amphiphilic compounds. See Kwetkat et al., U.S. Pat. No. 5,997,610. The hydrophilic portion of a demulsifier may contain formally charged residues—e.g. cationic, anionic, zwiterionic residues—or it may contain uncharged, polarized residues. The hydrophobic portion of a demulsifier may include long alkyl functional groups (>7 carbons), alkyl aryl functional groups, petroleum derivatives or even polysiloxane functional groups.

In many applications an effective demulsifier should also be ashless, low foaming, effective over a broad range of temperatures, have a low viscosity, and inhibit corrosion. Such ashless demulsifiers may be based upon amine sulfonates, amine sulfates, amine phosphates, and amine carboxylates.

Two tests are used in the art to predict the general effectiveness of a compound as a demulsifier and corrosion inhibitor, the ASTM D-1401 and ASTM D-665 tests. A description of these tests may be found in the Annual Book of ASTM Standards, Vol. 05.01, incorporated herein. ASTM D-1401 tests the relative speed and extent of demulsification between different demulsifiers. ASTM D-665 tests the relative corrosion protection afforded by different demulsifiers.

The ASTM D-1401 test procedure calls for the mixing of 40 mL of an oil phase and 40 mL of an aqueous phase (typically deionized water), followed by a period to allow the phases to separate. The demulsifier concentration is not specified in the ASTM method, and through experience, 5% of the demulsifier in the oil provides adequate results. The results to ASTM D-1401 are usually expressed in the form O/W/E (T), where the O is the volume of the organic layer, W is the volume of the aqueous layer, E is the volume of the emulsion layer, and T is the time in 5 minute increments up to 60 minutes.

For comparison of demulsifiers, we defined Relative Performance by measuring the time to complete separation in one-minute intervals. If separation did not occur within 60 minutes, then the value reported was >60.

The ASTM D-665 test procedure determines if rust spots appear on a steel rod after 24 hours being immersed in a mixture of 300 mL of oil and 30 mL of DI water (Part A) or synthetic sea water (Part B). Through experience, a "Pass" for part A at the low treat level of 0.005% demonstrates good efficacy as a corrosion inhibitor.

In addition to above-mentioned general qualities, a demulsifier should have the best possible ASTM D-1401 score. Additionally, good ASTM D-655 performance is desirable.

DEFINITIONS

1. Functional Fluids: A fluid formulated to accomplish a defined goal or combination of goals, such as, but not limited to, cooling, lubrication, corrosion protection, energy transfer, hydraulic action, combustion, or providing a dielectric medium.
2. Emulsion: A mixture of two or more immiscible liquids, consisting of droplets in a continuous phase.
3. Ashless: A compound not containing any metallic elements.
4. Amphiphilic: Any compound consisting of at least one lyophobic portion and at least one lyophilic portion.
5. Lyophilic Portion: That part of a molecule having a relative attraction to the solvent.
6. Lyophobic Portion: That part of a molecule having a relative repulsion to the solvent.
7. Hydrophilic Portion: The lyophilic portion when water is the solvent.
8. Hydrophobic Portion: The lyophobic portion when water is the solvent.
9. Alkyl Functional group: Any saturated or unsaturated, branched or unbranched hydrocarbon chain.
10. $C_8$–$C_{24}$ Alkyl Functional Group: An alkyl functional group consisting of from 8 to 24 carbons.
11. Aryl Functional Group: An aromatic ring or rings, such as, but not limited to benzene, toluene, xylene, naphthalene, or diphenyl oxide.
12. Alkyl Aryl Functional Group: An aryl functional group attached to one or more alkyl functional groups.
13. Alkyl Amine: An amine that contains one or more alkyl functional groups.
14. Alkyl Sulfonic Acid: A sulfonic acid with an alkyl functional group.
15. Alkyl Aryl Sulfonic Acid: A sulfonic acid with an alkyl aryl functional group.
16. Di-Alkyl Aryl Sulfonic Acid: A sulfonic acid with an aryl functional group that is attached to two alkyl functional groups.

17. Cocoyl Functional Group: A member of the set of linear, saturated or unsaturated hydrocarbon chains from 8 to 20 carbons.
18. Cocoyl Amines: An amine that contains one or more cocoyl functional groups.
19. Mono-Cocoyl Amine: An amine that contains one cocoyl functional group.
20. Di-Cocoyl Amine: An amine that contains two cocoyl functional groups.
21. Tri-Cocoyl Amine: An amine that contains three cocoyl functional groups.
22. Methyl, Di-Cocoyl Amine: A tertiary amine with one methyl functional group and two cocoyl functional groups.
23. Di-methyl, Cocoyl Amine: A tertiary amine with one cocoyl functional group and two methyl functional groups.
24. Polysiloxane Functional Group: A functional group containing a branched or unbranched silicon-oxygen backbone.
25. $C_8$–$C_{60}$ Alkyl Aryl Functional Group: An alkyl aryl functional group where the alkyl functional groups have a combined total of 8 to 60 carbon atoms.
26. Mono-$C_8$–$C_{24}$ Alkyl Benzene: A benzene ring that is attached to an alkyl functional group of 8 to 24 carbons.
27. Mono-$C_8$–$C_{24}$ Alkyl Toluene: A toluene ring that is attached to an alkyl functional group of 8 to 24 carbons.
28. Mono-$C_8$–$C_{24}$ Alkyl Xylene: A xylene ring is attached to an alkyl functional group of 8 to 24 carbons.
29. Di-$C_8$–$C_{24}$ Alkyl Toluene: A toluene ring that is attached to two alkyl functional groups of 8 to 24 carbons each.
30. Di-$C_8$–$C_{24}$ Alkyl Benzene: A benzene ring that is attached to two alkyl functional groups of 8 to 24 carbons each.
31. Organic System: Any organic solvent, oil, or combination of solvents, oils, and solutes.
32. Paraffinic Oil: A petroleum fraction that is predominately saturated hydrocarbons, commonly characterized by having a viscosity index greater than 100.
33. Naphthenic Oil: A petroleum fraction that contains some degree of unsaturation, commonly characterized by having a viscosity index less than 100.
34. Ester: An organic compound with one or more ester functional groups.
35. Mineral Oil: A petroleum fraction that is commonly obtained after the removal of compounds reactive toward sulfonating agents.
36. Poly Alpha Olefin: An oligomer of alpha olefins, typically decene.
37. Alkyl Aromatic Oil: A synthetic oil based on alkyl aryl groups.

SUMMARY OF THE INVENTION

The present invention is a corrosion inhibiting demulsifier and a method of breaking or inhibiting the formation of emulsions. A preferred demulsifier is formed from the salt of an amphiphilic amine and an amphiphilic acid with the general formula shown in Formula 1.

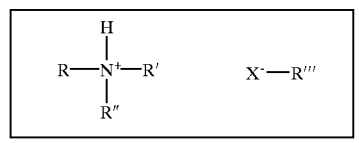

Formula 1

R, R', R" and R'" are functional groups. X is an acid. R, R', R" and R'" are chosen from the set of functional groups such that both the amine and acid portions of the molecule in Formula I are amphiphilic. In a preferred embodiment of the invention, the demulsifier may be a salt of an alkyl amine and an alkyl aryl sulfonic acid. Even more preferably, the demulsifier may be a salt of a methyl, di-cocoyl amine and an alkyl aryl sulfonic acid.

In a preferred amphiphilic amine, R is a $C_8$–$C_{24}$ alkyl functional group. R' and R" are each selected from a group consisting of: a hydrogen atom, a methyl functional group, a $C_8$–$C_{24}$ alkyl functional group, a benzene ring and an alkyl aryl functional group. In another preferable amine, R is a cocoyl functional group, and R' and R" are each selected from a group consisting of: a hydrogen atom, a methyl functional group and a cocoyl functional group. In yet another embodiment, R and R' are cocoyl functional groups, and R" is a methyl functional group.

Preferred functional groups for the acid include sulfonic acid, sulfuric acid, phosphoric acid, and carboxylic acid. The sulfonic acid may be derived from natural (such as, but not limited to, sulfonated petroleum oil) or synthetic (such as, but not limited to, alkyl aryl) sources. In a preferred sulfonic acid, R'" may be an alkyl aryl functional group. In another preferred embodiment, R'" may be an alkyl aryl functional group yielding a sulfonic acid with an average equivalent weight of about 500.

In another embodiment of the invention, the salt of an alkyl amine and an alkyl aryl sulfonic acid is added into an organic system to demulsify the system. In yet another embodiment of the invention, the salt of an alkyl amine and an alkyl aryl sulfonic acid is added to an organic system to inhibit the formation of an emulsion. In yet another embodiment of the invention, an oil-soluble amphiphilic amine is added to a naturally or synthetically based ester to inhibit formation of an emulsion or to demulsify an already emulsified system.

DETAILED DESCRIPTION OF THE INVENTION

The present invention is a demulsifying and corrosion-inhibiting compound formed from the salt of an amphiphilic amine and an amphiphilic acid with the general formula shown in Formula 1.

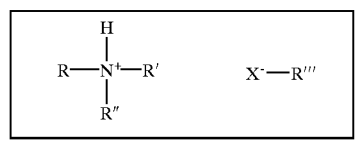

Formula 1

Table 1 relates the rate of demulsification as a function of alkyl chain length for the salt of a primary amine and an alkyl aryl sulfonic acid. The choice of preferred amines is a function of cost and performance. For example, in a weakly hygroscopic system, a slower demulsifier may be satisfactory. In a high temperature hydraulic system, maximum performance without regard to cost may be preferable. Accordingly, in a preferred amphiphilic amine, R is a $C_8$–$C_{24}$ alkyl functional group, benzene ring, or an alkyl aryl functional group. R' and R" are independently hydrogen atoms.

Table 1—Relative ASTM D-1401 Performance as a function of alkyl chain length for the salt of a primary amine and an alkyl aryl sulfonic acid

TABLE 1

Relative ASTM D-1401 Performance as a function of alkyl chain length for the salt of a primary amine and an alkyl aryl sulfonic acid

| Amine | Relative ASTM D-1401 Performance (min.) | Appearance of Water Layer |
|---|---|---|
| Ammonium | >60 | Opaque |
| n-Butyl | >60 | Opaque |
| n-Hexyl | >60 | Hazy |
| n-Octyl | 60 | Clear |
| n-Decyl | 11 | Clear |
| n-Dodecyl | 14 | Clear |
| n-Tetradecyl | 18 | Clear |
| n-Hexadecyl | 28 | Clear |
| n-Octadecyl | 60 | Clear |

Although n-decyl-dodecyl primary amines offer the maximum performance, there are significant cost advantages to employing cocoyl amines.

Table 2 demonstrates that among the tertiary amines, the di-cocoyl amines are preferable to the mono-cocoyl or tri-cocoyl amines if the rate of demulsification is the primary concern. It also teaches that if ASTM D-665 performance is critical, the di-methyl, cocoyl amine is preferable to the di-cocoyl and tri-cocoyl amines. Accordingly, in another preferred embodiment R is selected from the group consisting of: a $C_8$–$C_{24}$ alkyl functional group, a benzene ring, and an alkyl aryl functional group. R' and R" are each selected from a group consisting of: a methyl functional group, a $C_8$–$C_{24}$ alkyl functional group, a benzene ring and an alkyl aryl functional group. In another preferable amine, R is a cocoyl functional group, and R' and R" are each selected from a group consisting of: a hydrogen atom, a methyl functional group or a cocoyl functional group. In yet another embodiment, R and R' are cocoyl functional groups, and R" is a methyl functional group.

Table 2—Relative ASTM D-1401 and ASTM D-665 Part A performance as a function of substitution of the Amine for an amine neutralized with an alkyl aryl sulfonic acid with an equivalent weight of about 500.

TABLE 2

Relative ASTM D-1401 and ASTM D-665 Part A performance as a function of substitution of the amine for an amine neutralized with an alkyl arylsulfonic acid with an equivalent weight of about 500.

| Amine | Relative ASTM D-1401 Performance (Min.) | ASTM D-665 Part A |
|---|---|---|
| Ammonium | >60 | Pass |
| Dimethyl, Cocoyl | 13 | Pass |
| Methyl, Di-cocoyl | 10 | Fail |
| Tri-cocoyl | 30 | Fail |

Accordingly, in a preferred amphiphilic amine, selected without regard to ASTM D-665 performance, R is a cocoyl functional group, and R' and R" are each a hydrogen atom, a methyl functional group or a cocoyl functional group. In another embodiment, R and R' are cocoyl functional groups, and R" is a methyl functional group. If ASTM D-665 performance is critical, in a preferred amine, R is a cocoyl functional group and R' and R" are each a hydrogen atom or a methyl functional group.

Table 3 relates the relative ASTM D-1401 performance as a function of the equivalent weight of a sulfonic acid in a demulsifier formed from the salt of a tertiary amine and an alkyl aryl sulfonic acid. Table 3 suggests that the rate of demulsification of an alkyl aryl substituted sulfonic acid is dependent on the composition of the alkyl aryl functional group. As one skilled in the art may appreciate, these trends should be similar for any substituted acid provided the polarity of the substituted acid is comparable to the polarity of an alkyl aryl substituted sulfonic acid.

Table 3. Relative ASTM D-1401 performance of Various Aryl Sulfonic Acids Neutralized with the Methyl, Di-Cocoyl Amine.

TABLE 3

Relative ASTM D-1401 performance of Various Aryl Sulfonic AcidsNeutralized with the Methyl, Di-Cocoyl Amine.

| Approximate Sulfonic Acid Equivalent Weight | Alkyl Chain Structure | Relative ASTM Structure D-1401 Performance (Min.) |
|---|---|---|
| 186 | Di-methyl | >60 |
| 320 | Branched | 18 |
| 320 | Linear | 31 |
| 500 | Mono-Linear | 20 |
| 500 | Di-Linear | 10 |

Accordingly, a preferred amphiphilic acid is an oil soluble sulfonic acid. The oil soluble sulfonic acid may be either synthetically derived, such as from sulfonated alkyl aryl groups, or naturally derived, such as from sulfonated petroleum oils. Accordingly, in another embodiment of the invention, an alkyl sulfonic acid with an equivalent weight of 300 to 600 is preferred. In a still more preferable embodiment, an alkyl aryl sulfonic acid with an average equivalent weight of 500 may be employed.

Salts of an amphiphilic amine and an amphiphilic acid can be prepared by a variety of methods well known in the art. The most preferable method is to combine approximately equimolar quantities of the acid and amine in an approximately equal weight of diluent oil. The order and rates of addition are not critical, and matter only in practical applications where there are system limits on the temperature rise that can be tolerated. A slight excess of the amine is often used to achieve an alkaline environment, common to most functional fluids. The functions of the diluent oil are to lower the product viscosity and to moderate the heat generated. To further control the heat evolution, the diluent oil and acid can be mixed, and the amine added at a rate such that the temperature rise is controlled (the acid can also be added to the oil/amine mixture without affecting the final properties). It is appreciated by those skilled in the art that there are many methods for producing neutral sulfonates, and with proper equipment, the incorporation of the diluent oil is not required.

Alternatively, though less preferably, the amphiphilic salt may be formed by mixing a neutral amine salt and a neutral sulfonate. If either di-methyl, cocoyl amine sulfate or a sodium sulfonate with an equivalent weight of approximately 520 is added to the oil-water mixture, an emulsion is formed. However, when di-methyl, cocoyl amine sulfate was mixed with the above sodium sulfonate, the oil-water system was demulsified but the oil and water were opaque.

An emerging trend in functional-fluid engineering is the use of esters for base oils. One of the barriers to more widespread adoption of this technology is finding a suitable demulsification scheme. Conventional demulsifiers quickly lose efficacy in esters. The mechanism is not completely understood, but it is presumed that ester hydrolysis yields amphiphilic organic acids that tend to stabilize emulsions. It follows that if an amphiphilic amine is added to an ester, it would neutralize any amphiphilic acid forming a compound consistent with the scope of this invention.

EXAMPLE 1
Preparation of a Demulsifier Based on a Di-methyl, Cocoyl Amine and a Di-alkyl Aryl Sulfonic Acid Diluent oil, such as SJR 100-HTS from San Joaquin Refining, 3129 Standard Street, Bakersfield, Calif. 93388, (43.1 grams) was placed into a 250 mL beaker containing a magnetic stir bar. An alkyl aryl sulfonic acid with an average molecular weight of about 500, such as Aristonic Acid 9800 from Pilot Chemical Corp., 11756 Burke Street, Santa Fe Springs, Calif. 90670 (38.8 grams), was then added to the beaker, and the components stirred until the mixture was homogeneous. Next, di-methyl, cocoyl amine, such as Armeen DMCD from Akzo Nobel, 8201 West $47^{th}$ Street, McCook, Ill. 60525 (18.1 grams), was added while mixing. An exotherm occurred, consistent with neutralization of the acid with the amine. In addition, the color of the mixture changed from a greenish tint consistent with sulfonic acid solutions, to a red-brown color consistent with a neutral sulfonate.

Next, 5 g of the above product was diluted with additional diluent oil (95 grams) to produce a 5% solution for ASTM D-1401 testing. Following the specified set-up and run procedures set forth in the ASTM D-1401 method, the oil phase and water phase completely separated in 13 minutes. In comparison, calcium sulfonate with demonstrated excellent demulsibility performance yielded a separation in 18 minutes. In both cases, at the time of separation, the oil phase was hazy, and the water phase was clear. A faster separation time suggests a better demulsibility performance.

Another portion of the product (0.025 grams) was diluted with additional diluent oil (500 grams) to generate the 0.005% solution by weight for evaluation by ASTM D-665, part A. The product passed.

EXAMPLE 2
Preparation of a Demulsifier Based on a Methyl, Di-cocoyl Amine and a Di-alkyl Aryl Sulfonic Acid by Metathesis A sample of Aristonate U, a neutral sodium sulfonate from Pilot Chemical Corp. (200 grams, 60% active, 475 average equivalent weight) and Armeen M2C, a methyl, di-cocoyl amine from Akzo Nobel, (102 grams) were dissolved into toluene (200 grams). Water (200 grams) was then added, and the mixture stirred. The homogeneous mixture was then allowed to settle into an upper organic phase that contained the desired product and a lower aqueous phase that contained most of the sodium (likely as sodium hydroxide) produced by the metathesis. After removing the lower, aqueous phase, another aliquot of water (200 grams) was added, the mixture stirred, then allowed to settle. The product was then recovered by removing the lower phase, and stripping the upper phase of the volatile solvents.

EXAMPLE 3
Demulsification of Soluble Oil by the Addition of a Demulsifier Based on a Methyl, Di-cocoyl Amine and a Di-alkyl Sulfonic Acid A stable emulsion formed by mixing 5% by weight of a soluble oil consisting of (16% Aristonate M, 4% Caloxylate N-9, both from Pilot Chemical Company and the balance N100HTS diluent oil from San Joaquin Refining) in water was treated with 0.5% by mass (based on the total emulsion) of the compound in Example 1. After mixing, the solution was permitted to settle. The emulsion rapidly broke into a slightly hazy oil layer, a cream layer, and an opaque lower layer.

EXAMPLE 4
Enhancement of the Demulsification of High Oleic Safflower Oil (A Partially Hydrolyzed Ester) by Addition of a Di-methyl, Cocoyl Amine Four samples were prepared consisting of 95 grams high oleic safflower oil (California Oils Corporation, 1145 Harbour Way South, Richmond, Calif. 94804), and 5 grams of demulsifying compound. Samples 1 and 2 contained calcium alkyl aryl sulfonate (Aristonate C-5000 from Pilot Chemical Corp.), a standard demulsifier, samples 3 and 4 contained the compound in Example 1. Samples 1 and 3 were evaluated with ASTM D-1401 testing. Sample 1 demulsified in 21 minutes. Sample 3 demulsified in about 12 minutes. Next, 0.5 g of water was added to Samples 2 and 4, the mixture was stirred and heated to 50° C., and kept overnight to demonstrate efficacy loss in typical applications. ASTM D-1401 testing of a portion of Samples 2 and 4 showed the complete phase separation after 45 and 40 minutes, respectively. Next, 0.5 grams of di-methyl cocoyl amine (Armeen DMCD, from Akzo Nobel) was then added to remainders of Samples 2 and 4, the mixtures were stirred and ASTM D-1401 performance of each was evaluated. Sample 2 phase separated in 25 minutes; Sample 4 separated in 15 minutes.

What is claimed is:

1. A method of demulsifying an emulsion comprising mixing said emulsion with a demulsifier compound, wherein the demulsifier compound comprises a salt of an amphiphilic amine and an amphiphilic acid of the general Formula 1,

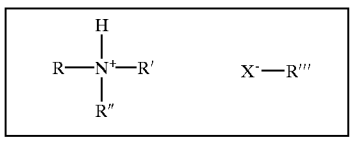

Formula 1 wherein:
(a) R' and R" are each selected from the group consisting of: a hydrogen atom, a methyl functional group, a $C_8$–$C_{24}$ alkyl functional group, a benzene ring and an alkyl aryl functional group;
(b) R and R'" are each selected from the group consisting of: a $C_8$–$C_{24}$ alkyl functional group, an alkyl aryl functional group, and a polysiloxane functional group; and
(c) X is selected from the group of acids consisting of: sulfonic acid, sulfuric acid, carboxylic acid, and phosphoric acid.

2. The method of claim 1 wherein said amphiphilic acid is an alkyl aryl sulfonic acid.

3. The method of claim 2, wherein said alkyl aryl sulfonic acid has an equivalent weight from 300 to 600.

4. The method of claim 1, wherein said emulsion is a mixture of a functional fluid with water or a polar solvent.

5. The method of claim 4 wherein the demulsifier compound is dissolved in said functional fluid in a concentration less than 5% and more than 0.01% by weight.

6. The method of claim 1, wherein
(a) R is selected from the group of linear, completely saturated alkyl chains with 8 to 18 carbons,
(b) R' and R" are each hydrogen atoms,
(c) R'" is an alkyl aryl functional group, and
(d) X is a sulfonic acid.

7. The method of claim 1, wherein
(a) R is a methyl functional group,
(b) R' and R" are cocoyl functional groups,
(c) R'" is an alkyl aryl functional group, and
(d) X is a sulfonic acid.

8. The method of claim 1, wherein
(a) R and R' are methyl functional groups,
(b) R" is a cocoyl functional group,
(c) R'" is an alkyl aryl functional group, and
(d) X is a sulfonic acid.

9. The method of claim 1, wherein
(a) R, R', and R" are cocoyl functional groups,
(b) R'" is an alkyl aryl functional group, and
(c) X is a sulfonic acid.

10. A method of inhibiting the formation of an emulsion comprising mixing an organic system with an emulsion inhibiting compound, wherein the emulsion inhibiting compound comprises a salt of an amphiphilic amine and an amphiphilic acid of general Formula 1

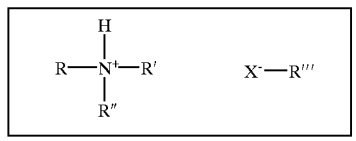

Formula 1 wherein:
(a) R' and R" are each selected from the group consisting of: a hydrogen atom, a methyl functional group, a $C_8$–$C_{24}$ alkyl functional group, a benzene ring and an alkyl aryl functional group;
(b) R and R'" are each selected from the group consisting of: a $C_8$–$C_{24}$ alkyl functional group, an alkyl aryl functional group, and a polysiloxane functional group; and
(c) X is selected from the group of acids consisting of: sulfonic acid, sulfuric acid, carboxylic acid, and phosphoric acid.

11. The method of claim 10 wherein said amphiphilic acid is an alkyl aryl sulfonic acid.

12. The method of claim 11, wherein said alkyl aryl sulfonic acid has an equivalent weight from 300 to 600.

13. The method of claim 10, wherein said emulsion is a mixture of a functional fluid with water or a polar solvent.

14. The method of claim 13 wherein the emulsion inhibiting compound is dissolved in said functional fluid in a concentration less than 5% and more than 0.01% by weight.

15. The method of claim 10, wherein
(a) R is selected from the group of linear, completely saturated alkyl chains with 8 to 18 carbons,
(b) R' and R" are each hydrogen atoms,
(c) R'" is an alkyl aryl functional group, and
(d) X is a sulfonic acid.

16. The method of claim 10, wherein
(a) R is a methyl functional group,
(b) R' and R" are cocoyl functional groups,
(c) R'" is an alkyl aryl functional group, and
(d) X is a sulfonic acid.

17. The method of claim 10, wherein
(a) R and R' are methyl functional groups,
(b) R" is a cocoyl functional group,
(c) R'" is an alkyl aryl functional group, and
(d) X is a sulfonic acid.

18. The method of claim 10, wherein
(a) R, R', and R" are cocoyl functional groups,
(b) R'" is an alkyl aryl functional group, and
(c) X is a sulfonic acid.

19. The method of claim 10, wherein said organic system includes paraffinic oil, naphthenic oil, mineral oil, poly alpha olefin, or alkyl aromatic oil.

20. The method of claim 1 wherein the emulsion comprises an ester emulsion.

21. A method of demulsifying an ester emulsion comprising mixing an amphiphilic amine with an ester emulsion wherein said amphiphilic amine is added in a quantity sufficient to neutralize excess amphiphilic acid present in the ester emulsion and wherein said amphiphilic amine comprises general Formula 2,

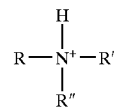

Formula 2 wherein:
(a) R' and R" are each selected from the group consisting of: a hydrogen atom, a methyl functional group, a $C_8$–$C_{24}$ alkyl functional group, a benzene ring and an alkyl aryl functional group; and
(b) R is selected from the group consisting of: a $C_8$–$C_{24}$ alkyl functional group, an alkyl aryl functional group, and a polysiloxane functional group.

22. The method of claim 21 wherein said ester emulsion comprises a partially hydrolyzed amphiphilic acid ester-based functional fluid.

23. The method of claim 10 wherein the emulsion comprises an ester emulsion.

24. A method of inhibiting formation of an ester emulsion comprising mixing an amphiphilic amine with an ester such that a slight reserve of amphiphilic amine is maintained in the mixture and wherein said amphiphilic amine comprises general Formula 2,

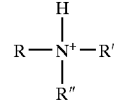

Formula 2 wherein:
(a) R' and R" are each selected from the group consisting of: a hydrogen atom, a methyl functional group, a $C_8$–$C_{24}$ alkyl functional group, a benzene ring and an alkyl aryl functional group; and
(b) R is selected from the group consisting of: a $C_8$–$C_{24}$ alkyl functional group, an alkyl aryl functional group, and a polysiloxane functional group.

25. The method of claim 24 wherein said ester comprises an amphiphilic acid ester-based functional fluid.

26. A method of demulsifying a partially hydrolized, amphiphilic acid ester-based functional fluid comprising mixing an amphiphilic amine with said functional fluid wherein said amphiphilic amine is added in a quantity sufficient to neutralize the amphiphilic acid present and wherein said amphiphilic amine comprises general Formula 2,

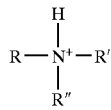

Formula 2 wherein:
(a) R' and R" are each selected from the group consisting of: a hydrogen atom, a methyl functional group, a $C_8$–$C_{24}$ alkyl functional group, a benzene ring and an alkyl aryl functional group; and
(b) R is selected from the group consisting of: a $C_8$–$C_{24}$ alkyl functional group, an alkyl aryl functional group, and a polysiloxane functional group.

27. A method to extend the emulsion prohibiting performance of an amphiphilic acid ester-based functional fluid comprising mixing an amphiphilic amine with said functional fluid such that a slight reserve of amphiphilic amine is maintained in the mixture and wherein said amphiphilic amine comprises general Formula 2,

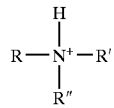

Formula 2 wherein:
(a) R' and R" are each selected from the group consisting of: a hydrogen atom, a methyl functional group, a $C_8$–$C_{24}$ alkyl functional group, a benzene ring and an alkyl aryl functional group; and
(b) R is selected from the group consisting of: a $C_8$–$C_{24}$ alkyl functional group, an alkyl aryl functional group, and a polysiloxane functional group.

* * * * *